United States Patent
Shau et al.

(10) Patent No.: US 8,047,993 B2
(45) Date of Patent: Nov. 1, 2011

(54) QUANTITATIVE NON-INVASIVE METHOD FOR DETECTING DEGREE OF MALIGNANCY IN TUMORS AND APPLICATION THEREOF

(75) Inventors: Yio-Wha Shau, Taipei (TW); Fon-Jou Hsieh, Taipei (TW); King-Jen Chang, Tua Yuan (TW); Sun-Hua Pao, Taipei (TW); Chiung-Nein Chen, Tainan Hsien (TW)

(73) Assignee: Industrial Technology Research Institute, Hsinchu (TW)

( * ) Notice: Subject to any disclaimer, the term of this patent is extended or adjusted under 35 U.S.C. 154(b) by 1946 days.

(21) Appl. No.: 11/099,570

(22) Filed: Apr. 6, 2005

(65) Prior Publication Data

US 2006/0241463 A1 Oct. 26, 2006

(51) Int. Cl.
*A61B 5/05* (2006.01)
*G06K 9/00* (2006.01)
(52) U.S. Cl. ........................................ 600/453; 382/128
(58) Field of Classification Search .................. 382/128, 382/131; 250/353.01; 345/650, 165, 661
See application file for complete search history.

(56) References Cited

U.S. PATENT DOCUMENTS

| 5,860,929 A | 1/1999 | Rubin et al. |
| 6,112,108 A | 8/2000 | Tepper et al. |
| 6,315,730 B1 | 11/2001 | Hoff et al. |
| 7,069,068 B1* | 6/2006 | Ostergaard .................... 600/420 |
| 7,113,817 B1* | 9/2006 | Winchester et al. .......... 600/476 |
| 2003/0050553 A1* | 3/2003 | Samoszuk et al. ............ 600/410 |

* cited by examiner

*Primary Examiner* — Tse Chen
*Assistant Examiner* — Helene Bor
(74) *Attorney, Agent, or Firm* — Birch, Stewart, Kolasch & Birch, LLP

(57) ABSTRACT

Disclosed is a method for detecting the degree of malignancy in tumors noninvasively, which comprises the steps of: using a Power Doppler ultrasound unit to scan a tumor and capture sequential color imagines in a complete heartbeat cycle, and choosing an area of interest (AREA_ROI) from the images; labeling pixels reflecting signals of bloodflow in the imagines during one heartbeat cycle to contour an area of tumor blood vessels (AREA_vessel); calculating a difference of PDVI between maximal systolic pressure and diastolic pressure during the heartbeat cycle to obtain tumor differential vascularity index (TDVI), in which PDVI is the ratio obtained by dividing pixels of AREA_vessel by a total area in the section of AREA_ROI; and determining the degree of malignancy by the TDVI. The method of the present invention can be applied to monitor the response of tumor to clinical treatment.

23 Claims, 5 Drawing Sheets
(2 of 5 Drawing Sheet(s) Filed in Color)

(A)

(B)

(C)

QUANTITATIVE NON-INVASIVE METHOD FOR DETECTING DEGREE OF MALIGNANCY IN TUMORS AND APPLICATION THEREOF

BACKGROUND OF THE INVENTION

1. Field of the Invention

The present invention relates to a method for assessment of tumors, especially relates to a novel method of non-invasive measurement of tumor hemodynamic parameters to detect the degree of malignancy in tumors.

2. The Prior Arts

Tumor blood flow plays an important role for tumor growth and metastasis from the view of tumor metabolism. It's also crucial to the selection of optimal therapy and a marker for response to therapy. Jain reviewed the current knowledge of physical parameters for normal, benign and malignant neoplastic tissues in Cancer Research, volume 48(10): 2641-58, 1988. Non-invasive techniques for assessment of tumors like magnetic resonance imaging (MRI), ultrasound B-Mode Image are known for imaging tumor sizes, structures of blood vessels in tumors, vascular network of tumor, integrity of tumor surface, resistance indices such as pulsed index (PI) and resistance index (RI), and so on. The outcomes of aforementioned detection are limited to suitability when compared with the results of invasive tumor sampling with blood vessel staining or with those of cell culture. This is due to many insufficient assumptions on detection of images and lack of precise quantification indexes, which results not enough credibility.

The degree of angiogenesis in tumors is closely related to the malignancy of tumors, even to the survival rate of therapy. During angiogenesis, microvascular endothelial cells proliferate rapidly which cause only single layer of endothelial cells in the neovascular wall. Consequently, the blood flow of neovasculature is significantly different from that of normal blood vessel under the action of pulsatile blood pressure. Therefore, detection of macroscopic or microscopic blood flow on the artery vessel wall for tumor growth and its hemodynamics are of important values.

Owing to the broad clinical applications of color Doppler ultrasound, one of the inventors of the present invention, Dr. Hsieh, Fon-Jou, published a paper: "Incremental angiogenesis assessed by color Doppler ultrasound in the tumorigenesis of ovarian neoplasms" in Cancer (1994, volume 73(4): 1251-6). The crucial role of angiogenesis in malignancy of ovarian neoplasms was confirmed with hemodynamic parameters of PI and RI by color Doppler ultrasound analysis. The following publications related to the clinical applications of color Doppler ultrasound analysis also proved the significance of hemodynamics between the development of cervical cancer and the effects of chemotherapy. U.S. Pat. No. 6,112,108 disclosed a method using Doppler technique to evaluate the nature of diastolic flow within tumors (the time-decay constant of a post-systolic tumor blood-flow waveform) as a means of inferring the vascular resistance, and thus the likelihood of malignancy.

People skilled in the art understand that arterial vessels in tumors are either difficult to locate or many vessels are found all at once. And the differences among vessels are quite significant which result in problems for carrying out the abovementioned method. There is therefore a need for an easy-to-diagnose method with more physical meanings for reliably and accurately assessing the likelihood of malignancy of tumors. Hsieh et al. first used vascularity index (VI) as a novel parameter for the in vivo assessment of angiogenesis in tumors with power Doppler imaging technique ("Usefulness of Doppler spectral analysis and power Doppler sonography in the differentiation of cervical lymphadenopathies." AJR Am J Roentgenol. 1998, Vol. 171(2):503-9). The concepts of PI and RI indices were extended to vascularity index (VI). VI is of great clinical value in classification of the stages in cervical carcinoma. The color Doppler vascularity index (CDVI) can represent the known quantitative vascular signals of color Doppler sonography. The CDVI is defined as the ratio of the number of the colored pixels (area for blood vessels on which blood stream can be detected by color Doppler ultrasound units) within a tumor section (Region of Interest, ROI) to the number of total pixels (area for tumor) in that specific tumor section during systolic stage. In other words, the CDVI reflects the ratio of running blood vessels inside the tumor. The value of CDVI is higher in the patients with malignant tumors or metastatic cancers. The CDVI can be defined by the following formula:

CDVI=the measure of color area in ROI/the measure of ROI area

And Power Doppler ultrasound (US) is superior to conventional color Doppler imaging in the detection of blood flow because of its high sensitivity to low flow rates in small vessels.

In addition, U.S. Pat. No. 5,860,929 described a method for quantitatively estimating the amount of tissue that contains moving blood in tissue for a region of interest using power Doppler ultrasound. The power Doppler image of the soft tissue blood volume is scanned in fixed time interval from a frozen image (Frozen ROI). When a pixel value with a power level is greater than the particular intensity threshold, the Doppler power level of said pixel will be summed to the total power level. The fractional moving blood volume (FMBV) is calculated by dividing the total power by the number of Reference Doppler Power Level and total pixels in the region of interest pixels (the measure of ROI area).

Even though the abovementioned methods provide a preliminary quantitative tool for tumor classification, tumors containing soft tissue and blood vessels are highly versatile which makes the representative frozen image difficult to take. In addition, no standardized threshold causes the range of CDVI parameter being limited to the function of scanner hardware or affected by the scanning parameters. People have suggested an addition of ultrasonic Contrast Agent to raise the resolution of blood stream in power Doppler. U.S. Pat. No. 6,315,730 even revealed an effective amount of an ultrasound contrast agent which is designed to be particularly sensitive to disruption by the initial ultrasound pulse(s), thereby limiting the intensity required for the initial ultrasound irradiation to obtain a more accurate vascularity ratio. However, the improvement is still limited. Moreover, prior arts did not consider the interaction timing mechanism within tumor vascularity biomedical physics, which caused the goals of scientific and automatic diagnosis difficult to reach.

Although traditional vascularity index (VI) can be used to classify the tumor stage, the assessment of angiogenesis in tumors is preferred to be a better parameter for tumor development, malignancy and metastasis. Since the blood supply in tumor varies with the contents of arterial vessels and venous vessels in vivo, using only total VI of tumor to classify the tumor stage is not accurate enough physiologically.

In addition, the CDVI parameter determined by the known techniques is easily affected by scanning range (ROI). When the borderline of tumor is not significant clear, the measure errors due to sampling of section will affect seriously in the value of CDVI. And the known method used to choose the single image is fixed in the maximal systole. The image chosen may not be representative, and the total blood vessel areas measured are not necessarily right. Because the blood stream is continuously flowing, the area of Doppler images during the whole heartbeat cycle should be considered.

SUMMARY OF THE INVENTION

A primary object of the present invention is to provide a non-invasive method detecting tumor vascularity in a complete heartbeat cycle through a technique of Power Doppler sonography to obtain a useful parameter for assessment of tumor development, metastasis, and the degree of malignancy.

To fulfill the objective of the present invention, the method for detecting the degree of malignancy in tumors according to the invention comprises the steps of:

(1) using a Power Doppler ultrasound unit to scan a tumor and capture sequential color images in a complete heartbeat cycle, and choosing an area of interest (AREA_ROI) from the images;
(2) labeling pixels reflecting signals of bloodflow during one heartbeat cycle to obtain an area of tumor blood vessels (AREA_vessel);
(3) calculating a difference of PDVI between maximal systolic pressure and diastolic pressure during the heartbeat cycle to obtain tumor differential vascularity index (TDVI), and the PDVI is a ratio obtained by dividing the pixels of AREA_vessel by the total area in that section of AREA_ROI; and
(4) determining a degree of malignancy by the TDVI.

The PDVIs of systolic pressure and diastolic pressure in heart have a difference expressed as the TDVI. The location with TDVI represents a group of blood vessels with low perfusion in the tumor region. The reflection signals of blood flow in the location will appear in systolic phase but not in diastolic phase due to low perfusion. The TDVI is defined as the ratio of the number of the pixels to the area of the tumor section. Low perfusion and obvious pulsation due to the soft wall, small vessel diameters of the new blood vessels, and the tortuous vessels for tumor have made TDVI a good indicator for the area ratio of new blood vessels. Thus, the higher TDVI, the more tumor neovascularization exists, which also reflects the higher degree of tumor malignancy.

There is obvious difference between arterial pulsation and venous pulsation in tumor blood vessels. For example, during Power Doppler ultrasound measurements, the Power Doppler signals detected from artery are affected accordingly with the changes of blood pressure. However, veins contain more red blood cells and the changes of venous pulsation are not so obvious, which cause the Power Doppler signals in veins stay in a high value. The arterial area (AREA_artery) and venous area (AREA_vein) can therefore be calculated respectively after the arteries and veins in the tumor section are differentiated. The power Doppler vascular index of artery (PDVI_artery) and power Doppler vascular index of vein (PDVI_vein) are determined from the arterial area, venous area and the area of interest in tumor section (AREA_ROI) as listed below:

(1) Power Doppler vascular index of artery (PDVI_artery)= the arterial area (AREA_artery)/the area of interest in tumor section (AREA_ROI);
(2) Power Doppler vascular index of vein (PDVI_vein)=the venous area (AREA_vein)/the area of interest in tumor section (AREA_ROI).

If the area of interest in tumor section (AREA_ROI) was replaced with the area of tumor blood vessels (AREA_vessel) as the denominator, then the vessel density ratio (VDR) of artery and vein can be obtained respectively:

(3) the tumor artery Power Doppler density ratio (PVDR_artery)=the arterial area (AREA_artery)/the area of tumor blood vessels (AREA_vessel);
(4) the tumor venous Power Doppler density ratio (PVDR_vein)=the venous area (AREA_vein)/the area of tumor blood vessels (AREA_vessel).

To improve the accuracy of degree of malignancy indication of TDVI, the location of blood vessel nest after the abovementioned TDVI screening can be furthered differentiated between arteries and veins according to the pulsation of Power Doppler signals. The arterial or venous vessel density ratios of TDVI location can be calculated by TDVI areas of arteries and veins (TDVI_artery vs TDVI_vein). Analysis on these indices can be used to improve the accuracy for degree of malignancy determined by TDVI, and the definitions are listed below:

(5) the arterial vessel density ratio of TDVI (TVDR_artery)= TDVI areas of arteries (TDVI_artery)/the area of tumor blood vessels (AREA_vessel);
(6) the venous vessel density ratio of TDVI (TVDR_vein)= TDVI areas of veins (TDVI_vein)/the area of tumor blood vessels (AREA_vessel).

On the other hand, the neovascular arterioles are not like cooped vessels which contain extracellular matrixes formed of smooth muscle cells. This relative lack of muscle in these blood vessels leads to low-resistance flow. Therefore, neovascular blood vessels, no matter arteries or veins, have better interaction with arteries supplying blood (low resistance) which make the neovascular blood flow different from that of cooped vessels. In another word, the Power Doppler signals in the location of tumor neovascular nest regions followed the pulsation of heartbeat cycle, are not only highly correlated with the pulsation of the supplying arteries, but are relatively high in maximum rate of change of Power Doppler signal waveform during unit time. Therefore, the neovascular area (AREA_angio) can be further calculated from blood vessel nest screened with TDVI.

From this neovascualr area, the Angiogenesis Index (AI) and the Angiogenesis Vessel Density Ratio (AVDR) can be defined below:

(7) Angiogenesis Index (AI)=the neovascular area (AREA_angio)/the area of interest in tumor section (AREA_ROI);
(8) Angiogenesis Vessel Density Ratio (AVDR)=the neovascular area (AREA_angio)/the area of tumor blood vessels (AREA_vessel).

In general, tumor contains both cooped arteries (high resistance area) and neovascular blood vessels (low resistance area). The higher the ratio of neovascular blood vessels, namely the higher the ratio of low resistance area, and the higher the chance of malignant tumor. Consequently, the Angiogenesis Index (AI) and the Angiogenesis Vessel Density Ratio (AVDR) can be used to further improve the accuracy of tumor malignancy detected by TDVI. In addition, the tumor detection method provided by the present invention can be a real-time monitoring tool in prognosis assessment, and be helpful in stratifying patients for proper therapy.

BRIEF DESCRIPTION OF THE DRAWINGS

The patent or application file contains at least one drawing executed in color. Copies of this patent or patent application publication with color drawing(s) will be provided by the office upon request and payment of the necessary fee.

DETAILED DESCRIPTION OF THE PREFERRED EMBODIMENT

Figure 1:
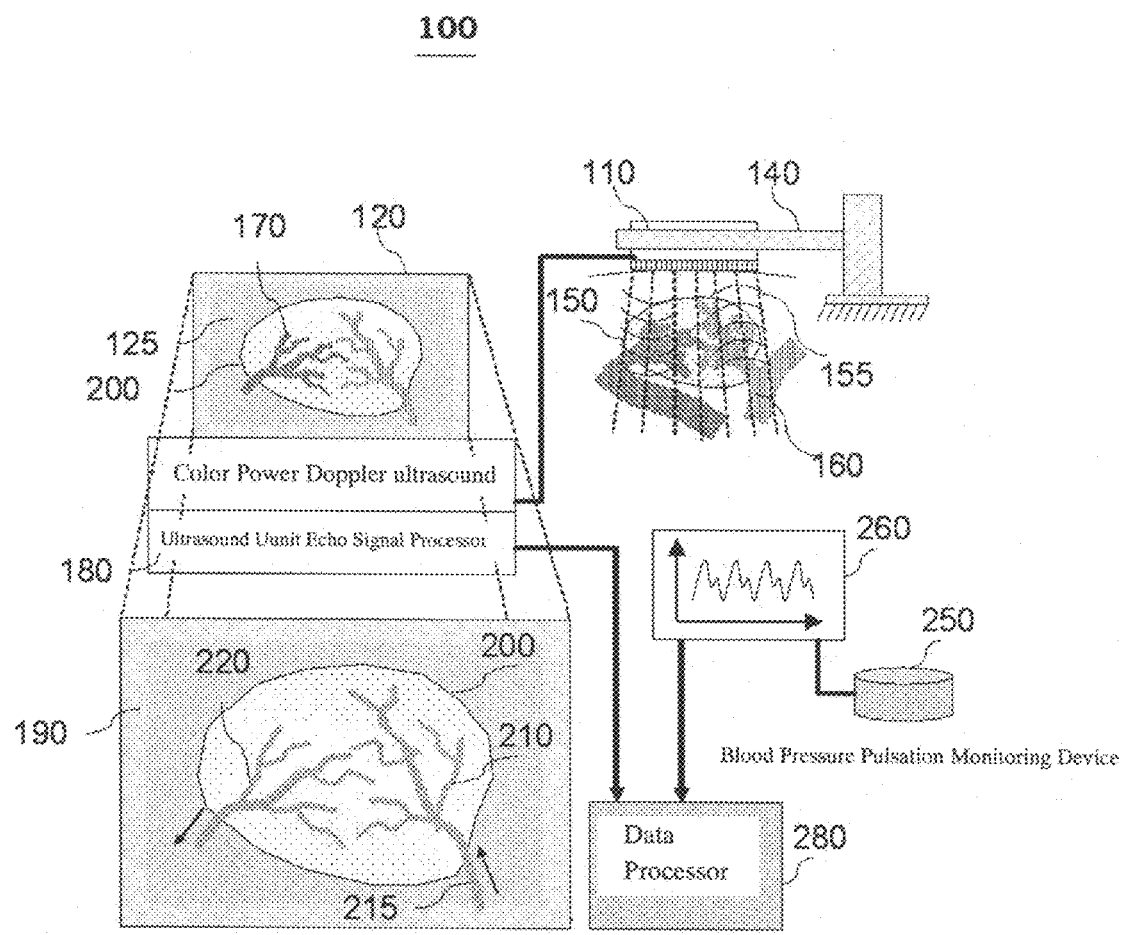
FIG. 1 depicts an embodiment of a system for measurement of tumor blood fluid mechanics parameters in accordance with the present invention.

People who skilled in the art will understand the invention with the related drawings in connection with the detailed description of the present invention which described briefly as follows, in which:

FIG. 1 depicts an embodiment of the system for measurement of tumor biomedical fluid mechanics parameters of the present invention. The system comprises a Color Power Doppler ultrasound unit 100 for providing images of tumor sections and angiographic Power Doppler images (such as HDI-5000 ultrasound unit) comprising an ultrasound probe 110 and a monitor 120. The ultrasound probe 110 can be moved in all 3-D directions to scan the whole tumor sections 125 for capturing representative images. An ultrasound probe fixer 140 can be used to locate the ultrasound probe 110 when the representative images are captured. The echo signals 155 will be different due to the differences of tissue density in living body when the oscillating pressure waves 150 reach the tumor region 160. Color Power Doppler ultrasound will generate a timing difference between the echo signals and the emitting signals from different sites into corresponding location and the echo signals can be transformed into gray scale display to reveal the relative form of tumor 170 in tumor region 160. In addition, the frequency changes of echo signals 155 and emitting signals 150 processed by the ultrasound unit echo signal processor 180 can build up the Power Doppler Image 190 in tumor region 160 through Doppler effects of moving red blood cells. The system of the present invention further comprises a blood pressure pulsation monitoring device 250 to provide arterial flow waveforms. The examples for blood pressure pulsation monitoring device include an air bag device for blood pressure measuring, and an ultrasound detecting device with M-model grey scale display, which provide the arterial diameter waveforms after analyzing the images from scanning the blood pressure changes of tumor providing arteries. The blood pressure pulsation monitoring device 250 is mounted in an artery of patient arm and the data from Color Power Doppler ultrasound unit 100 are taken at the same time for conveniently detection. The detecting system of the present invention records the information from real-time Power Doppler image 190 and blood pressure pulsation waveform signal 260 synchronously in the data processor 280 through a data transmission interface.

Next, a tumor section region of interest (ROI) 200 is selected among the Power Doppler images 190. The region 200 usually contains various tissues, such as blood vessels, which can be divided as arterial blood vessel nest 210 and venous blood vessel nest 220. And the nutrient for tumor tissue is supplied by one or many blood arteries 215 in tumor.

The method of the present invention provides a quantitative way for measuring area of micro capillaries in region of interest 200 and for calculating Power Doppler Vascularity Index (PDVI). The method can also quantify the areas of arterial or venous blood vessel nest 210/220 respectively and calculate each of the ratio of tumor arteries or veins to total blood vessels.

Figure 2:
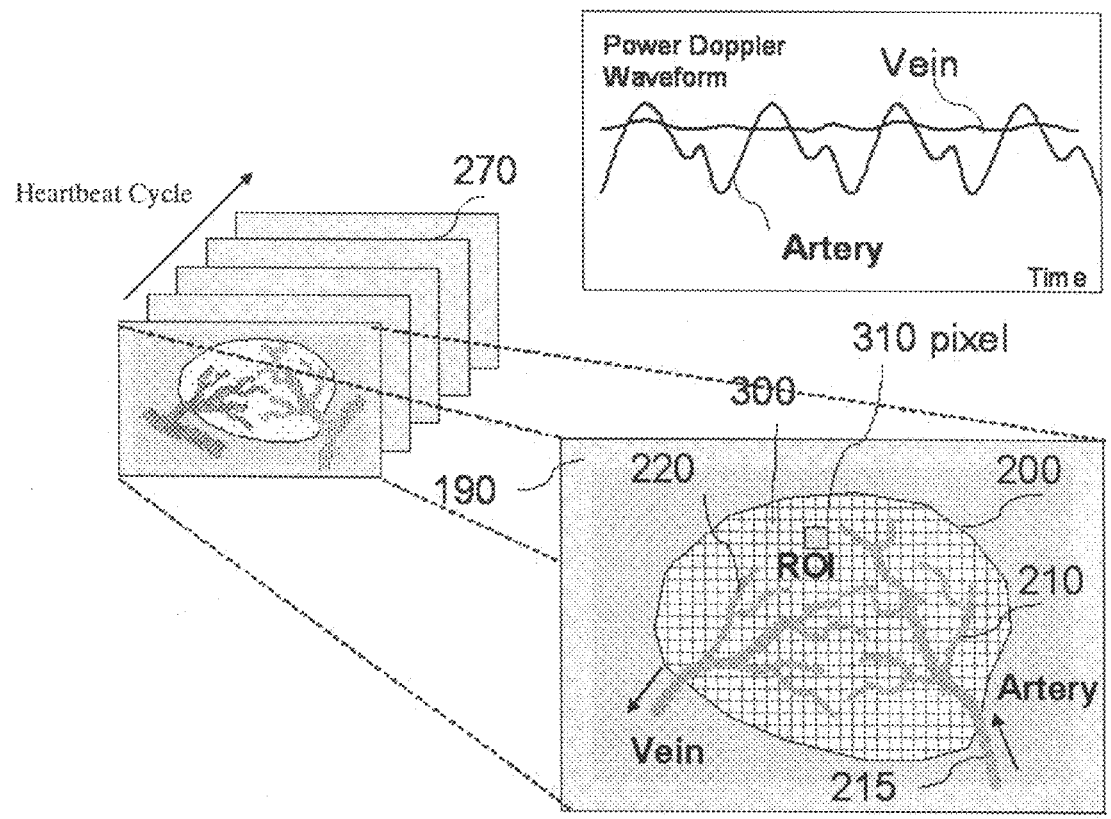
FIG. 2 illustrates diagrams of Power Doppler images of tumor ultrasound analysis.

FIG. 2 shows a diagram of Power Doppler image 190. The Power Doppler images 190 are obtained from ultrasonic image set or animation 270 in sequential Power Doppler ultrasound images from at least a complete heartbeat cycle. Tumor image are divided into a plurality of pixels 310 in the selected region of interest in tumor section 200 in digital image window 300. For example, the pixels of each color ultrasonic image in image set or animation are spilt into standard RGB or YIQ formats, and from these color scales values of RGB or YIQ values to build up the ratio of Power Doppler flow and calculate the area of blood vessels.

Figure 3:
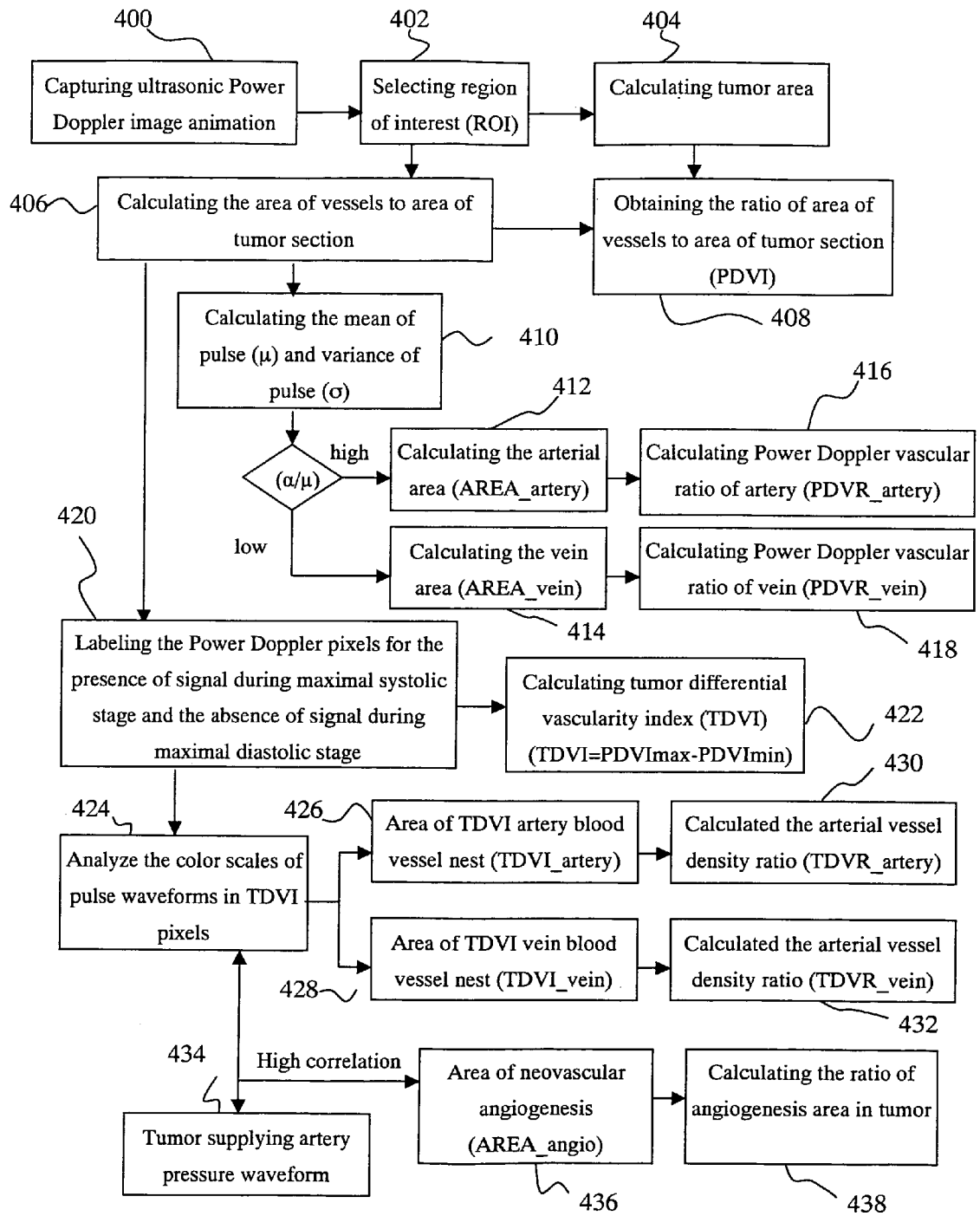
FIG. 3 shows a brief flow chart illustrating a method for tumor blood flow detection in accordance with the present invention.

FIG. 3 is a flow chart of the detecting method of the present invention. First at all, the tumor ultrasonic Power Doppler image animation is captured from the aforementioned system 400. After correcting the ultrasonic image with a depth scale, a proper region of interest is selected 402, and contoured to obtain quantified tumor area (AREA_ROI) 404. The regions with moving red blood cells in blood vessels will be shown in red pixels (pixels for blood flow reflection). Because the reaction of arterial flow are more rapid than the venous flow, the total area for cross-section of tumor should be observed in a complete heartbeat cycle but not from maximal pulse in systolic stage. The blood stream will flow in proper sequence through the blood vessel nests, therefore, each red bright pixel will be added up from systole to diastole during one complete heartbeat cycle to quantify the area of vessels 406 to area of tumor section, and thus obtaining the ratio of area of vessels to area of tumor section 408. Power Doppler Vascularity Index (PDVI) is also calculated. The PDVI is different from the disclosed in prior arts, which is calculated by adding all the red bright pixels (that is, total area for blood vessels: AREA_vessel) in one complete heartbeat cycle. While others select the red pixels from single image in maximal systolic stage, which do not express the real area of tumor blood vessels. A formula representing PDVI is shown as follow:

$$PDVI=AREA\_vessel/AREA\_ROI$$

On the other hand, the red blood cells in vessels will be reflected in red scale with Power Doppler ultrasound, the brightness of each red pixel will be changed in the blood vessel region corresponding to the fluctuation of heartbeat cycle. The number of red blood cells will be more in veins than in arteries, therefore the red scale will be maintained in high scale for veins. Also, the venous walls extend a little because of the venous pulse pressure, which will change the strength of Power Doppler signals. Therefore, the pulsation of veins is significant different form that of arteries. The flow of arterial Power Doppler will increase during systolic stage, which will make both the color Power Doppler area and brightness increase. But at the end of diastolic stage, usually the blood flow will be minimal and the strength and color of Power Doppler signals will be very small, or even to be invisible. The areas of Power Doppler pulsation in arterioles nest vary a lot, and the Doppler Intensities in arterial sites also varies much. Therefore, the variances of arterial Doppler intensities are many folds higher than those of veins (as shown in FIG. 2). Usually the Doppler's red scale in venous area is higher than averaged red scale, and the Doppler's red scale in arterial area is lower. Therefore, the method of the present invention calculates the mean of pulse ($\mu$) and variance of pulse (σ) 410. A ratio of variance to mean (σ/μ) of red scale is set to compare with a predetermined threshold value. If the ratio is larger than the threshold value, the site is labeled as arterial nest. Each pixel in arterial nest can be summed up to calculate the arterial area (AREA_artery) 412. On the contrary, the site is labeled as venous nest when the ratio is lower than the threshold value. Each pixel in venous nest can be summed up to calculate the venous area (AREA_vein) 414.

The ratio of tumor artery can be calculated according to Power Doppler intensity to obtain Power Doppler Vascular Index of artery (PDVI_artery) and Power Doppler Vascular Ratio of artery (PDVR_artery) 416. The ratio of tumor vein can be calculated to obtain Power Doppler Vascular Index of vein (PDVI_vein) and Power Doppler Vascular Ratio of vein (PDVR_vein) 418. The definitions of these two types of indices and ratios are described below:

(1) Power Doppler vascular index of artery (PDVI_artery)= the arterial area (AREA_artery)/the area of tumor section (AREA_ROI);
(2) Power Doppler vascular index of vein (PDVI_vein)=the venous area (AREA_vein)/the area of tumor section (AREA_ROI).
(3) the tumor artery Power Doppler density ratio (PVDR_artery)=the arterial area (AREA_artery)/the area of tumor blood vessels (AREA_vessel);
(4) the tumor venous Power Doppler density ratio (PVDR_vein)=the venous area (AREA_vein)/the area of tumor blood vessels (AREA_vessel).

Besides, according to previous description, the flow characteristics caused by pressure pulse in different blood vessels are different, and the area determined by Power Doppler will also be various. All the Power Doppler pixels in tumor region can be labeled for the presence of signal during maximal systolic stage and the absence of signal during maximal diastolic stage 420. Usually, PDVImax about maximal vessel area can be detected during maximal systolic stage and PDVImin about minimal vessel area can be detected during minimal diastolic stage. Tumor Differential Vascularity Index (TDVI) is obtained by subtracting PDVImin from PDVImax 422. The TDVI is a ratio of area of all the Power Doppler pixels for the presence of signal during maximal systolic stage and the absence of signal during maximal diastolic stage relative to the area of tumor section.

The pixel location calculated with TDVI represents a group of blood vessels with low perfusion in the tumor region; the reflection signals of blood flow in the location will appear in systolic phase (PDVImax is obtained in systolic phase) but not in diastolic phase (PDVImin is obtained in diastolic phase). The characteristics for new blood vessels of tumor such as tortuous distribution, small vessel diameters, low perfusion, thin wall and obvious pulsation have made TDVI a good indicator for the area ratio of new blood vessels. TDVI can be used to evaluate the degree of malignancy of tumor, that is, the higher TDVI, the more tumor neovascularization exists, which also reflects the higher degree of tumor malignancy.

According to the method of the present invention, TDVI index is not only used for evaluation of tumor malignancy but can be used to analyze the color scales of pulse waveforms in TDVI pixels in accordance with the pixels location calculated by TDVI 424. The TDVI vessel area in 420 can be separated into area of TDVI artery blood vessel nest (TDVI_artery) 426 and TDVI vein blood vessel nest (TDVI_vein) 428, and further calculated the arterial vessel density ratio (TDVR_artery) 430 and venous vessel density ratio (TDVR_vein) 432.

Analysis on those indices can be used to improve the accuracy for degree of malignancy determined by TDVI, and the definitions are listed below:

(5) the arterial vessel density ratio of TDVI (TVDR_artery)= TDVI areas of arteries (TDVI_artery)/the area of tumor blood vessels (AREA_vessel);
(6) the venous vessel density ratio of TDVI (TVDR_vein)= TDVI areas of veins (TDVI_vein)/the area of tumor blood vessels (AREA_vessel).

If the information of arterial flow waveforms or arterial diameter waveforms of tumor supplying artery are further included, the accuracy for determining artery and vein area can be further increased. For example, the waveform correlation between the waveform of Power Doppler Intensity changes in all the blood vessels of the tumor region (ROI) and tumor supplying artery pressure waveform 434 (upper arm artery pressure pulsation waveform) are analyzed (usually arterial blood vessel nest would have high correlation) and compared with a predetermined threshold. When the value of correlation (correlation coefficient) is higher than the threshold, this region will belong to the arterial area and is labeled as a part of AREA_artery. On the contrary, when the correlation of Power Doppler color scale and arterial pressure pulsation is low and the change of Power Doppler Intensity is also low, then this region will belong to the venous area and is labeled as AREA_vein.

On the other hand, the new blood vessel nest has thin walls, and is highly correlated with supplying artery. When the correlation between Power Doppler color scale of pulsation waveform of TDVI vessel area in 422 and pressure pulsation waveform is higher than the threshold, the area can be labeled as effective area of neovascular angiogenesis: AREA_angio 436. The area can also be determined with a spectrum analyzer. For example, when the spectrum of Power Doppler color scale of pulsation waveform of lower vessels is analyzed, the region can be labeled as area of neovascular angiogenesis (AREA_angio) if the ratio of the first harmonic frequency to total pulsation energy in the spectrum of that waveform region. Accordingly, the ratio of angiogenesis area in tumor can be calculated 438, such as the Angiogenesis Index (AI) and the Angiogenesis Vessel Density Ratio (AVDR), which can be defined below:

(7) Angiogenesis Index (AI)=the neovascular area (AREA_angio)/the area of tumor section (AREA_ROI);
(8) Angiogenesis Vessel Density Ratio (AVDR)=the neovascular area (AREA_angio)/the area of tumor blood vessels (AREA_vessel). And both AI and AVDR can be used to further improve the diagnostic accuracy of tumor malignancy detected by TDVI.

The size of cross-section of tumor contoured by Power Doppler does not affect the determination of TDVI. And the AI index is more accurate and representative than PDVI.

On the other hand, Power Doppler color scale of pulse waveform is obtained to distinguish the timing of diastolic notch, and the waveform is differential processed into digital signal to calculate the ratio of the time to the time of total heartbeat cycle, further to calculate the resistance coefficient of tumor blood fluid mechanics. When the ratio is smaller, the reflection point is closer, which also shows higher resistance. Usually the notch can not be observed due to the very high compliance of malignant tumor, which is one of the characteristics of low resistance. In general, tumor may contain both high resistance area and low resistance area. Therefore the higher the ratio of low resistance area is, the higher the chance of malignant tumor. Consequently, the resistance coefficient can also be used to further improve the accuracy of tumor malignancy detected by TDVI.

The method of the present invention provides effective parameters for tumor diagnosis and decreases the influence of hardware settings in ultrasonic measurement. The parameters establish a way to distinguish arteries, veins and neovascular densities, not only fit in the changeable characteristics of tumors, but also include the mechanisms of biophysics and blood fluid mechanics for malignant tumor detection. In addition, the non-invasive tumor detecting tools provided by the present invention are real-time monitoring tool in prognosis assessment, and are helpful in stratifying patients for proper therapy.

Example 1

Figure 4:
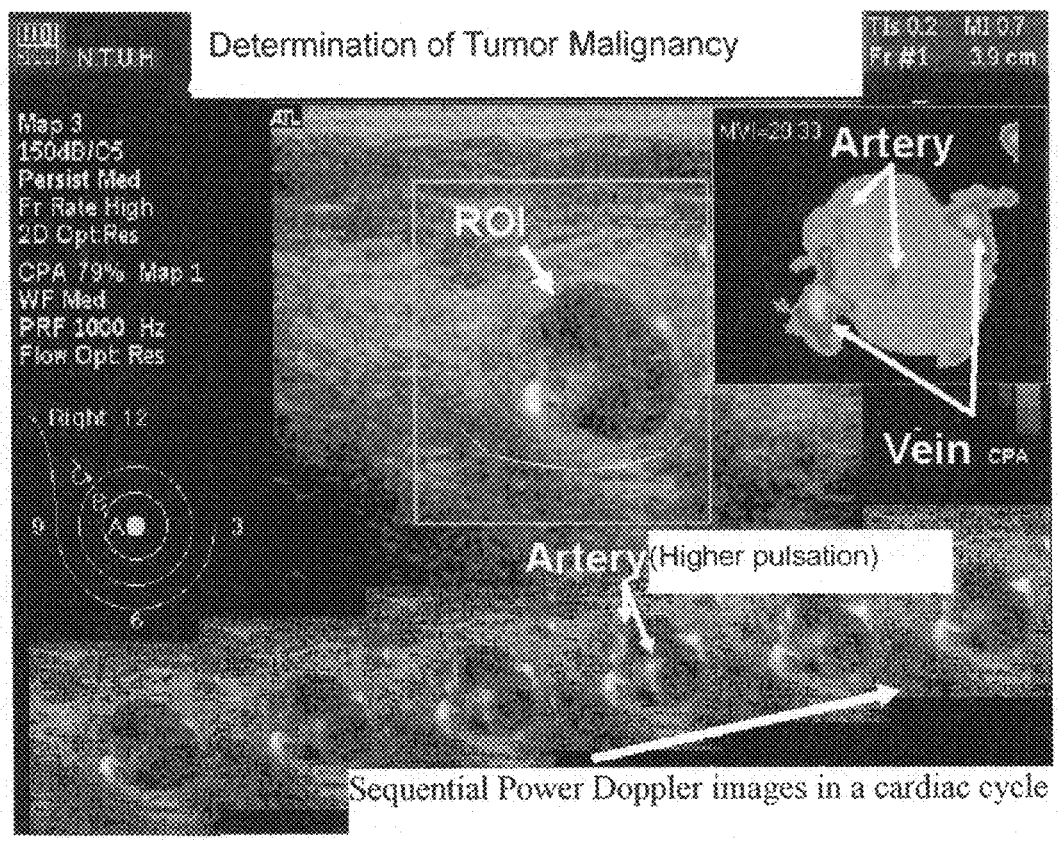
FIG. 4 is an embodiment showing a diagnosed result using the system of the present invention in breast tumor detection.

FIG. 4 is an embodiment showing a diagnosed result using the method of the present invention in breast tumor detection. The sequential Power Doppler images of the breast tumor are shown in the bottom. Middle square represents the margin of region of interest (ROI) and cross-section of blood vessel which is contoured by Power Doppler ultrasound. Upper right corner shows the results expressing arterial vessel nests and venous vessel nests in the tumor ROI cross-section distinguished with arrows by Power Doppler variance waveform analysis (upper right corner). The present invention uses the flow ultrasonic imaging analysis to study the interaction between tumor and pressure of supplying artery, to distinguish the PDVI arterial and venous regions in tumor, and to effectively calculate the degree of angiogenesis in tumor. The neovascular density ratio in tumor detected with ultrasound can be helpful in disease subtype classification, in stratifying patients for either enhance the chemical therapy or choose proper medication such as anti-angiogenesis drugs.

Example 2

Figure 5:
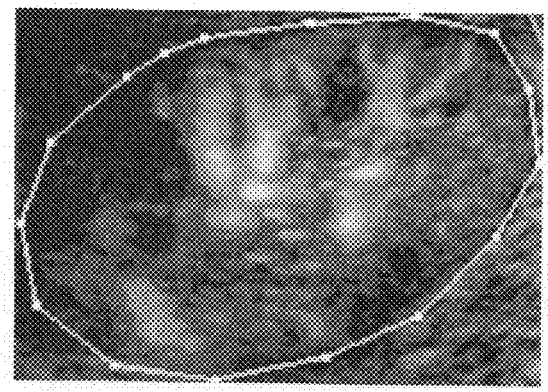
FIG. 5 is an embodiment showing a diagnosed result using the system of the present invention in kidney blood perfusion detection, the vessel pixels contributed to tumor differential vascularity index (TDVI) area are shown.
Figure 5:
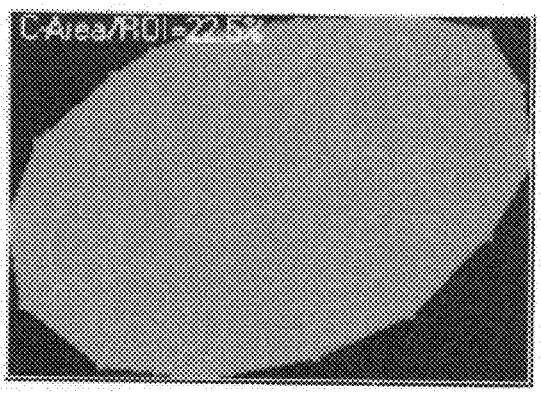
Figure 5:
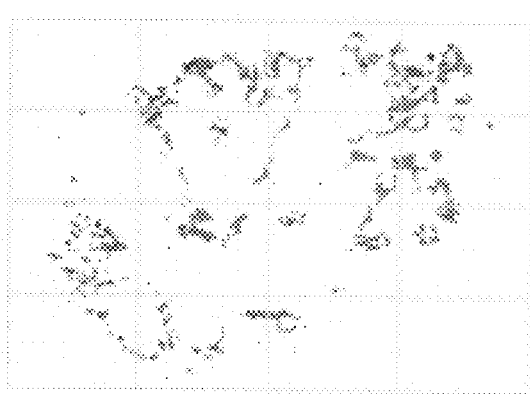

FIG. 5 is an embodiment showing a diagnosed result using the method of the present invention in kidney blood perfusion detection. The vessel pixels contributed to tumor differential vascularity index (TDVI) area are also shown. (A) represents the ultrasonic Power Doppler image during maximal systolic stage; (B) shows the Power Doppler pixels in tumor region which are higher than energy threshold during maximal systolic stage and lower than energy threshold during maximal diastolic stage; and (C) shows the difference of TDVI area in red scale. The pixel location calculated with TDVI represents a group of blood vessels with low perfusion (the reflection signals of blood flow in the location will appear in systolic phase but disappear in diastolic phase). New blood vessels of tumor have small vessel diameters, low perfusion, thin and soft wall, which have made TDVI a good indicator for the area ratio of new blood vessels. TDVI of the invention can further be used to represent the neovascular degree of tumor vessels.

Example 3

Thyroid cancer can be divided into 4 groups according to the tissue malignancy, which are described respectively below:
(1) Normal: tissues are sampled from another normal side of a thyroid tumor;
(2) Nodule Goitar (NG): patients usually require no operative intervention but sonography detection;
(3) Follicular Adenoma: lots of blood vessels proliferated in patients, the distinction between an adenoma versus a carcinoma is difficult, thyroidectomy is performed since carcinoma may be rendered from adenoma;
(4) Papillary thyroid carcinoma (PTC): tumor of malignancy.

A total of 53 patients with tumor are scanned with Doppler ultrasound in the tumor regions non-invasively. The CDVI, FMBV, PDVI indices from common use and the TDVI index in the present invention are analyzed to determine the degree of abnormality and aggressiveness of the cancer cells The tumor tissue sections are collected invasively and stained for endothelial cell CD34 antigen. Microvessels in the area are counted under microscope at 200× magnification. Three separate intense neovascular areas are assessed, and the mean is calculated as the microvessel density (MVD) of each tumor evaluated. Normal tissues are counted in the same way as a reference. Tumor tissues collected invasively are cultivated in vitro for 2 weeks to determine if excision of the tumor tissues is necessary (such as follicular adenoma and papillary thyroid carcinoma) or not (such as normal tissue and benign tumor).

The accuracies of each MVD, CDVI, FMBV, PDVI and TDVI indices in assessing the tumor malignancy are examined by t-test, and the P values are shown in Table 1. TDVI of the invention shows the best accuracy among the known non-invasive detection methods (P=0.0006). On the other hand, the method of the invention can be carried out in real-time, while conventional way of tissue culture needs 2 weeks to confirm the degree of tumor malignancy.

TABLE 1

Comparison of the accuracy of different detection indices

| Technique type | MVD | CDVI | FMBV | PDVI | TDVI |
|---|---|---|---|---|---|
| P-value | 0.015 | 0.055 | 016 | 0.029 | <0.001 |

Though the present invention is explained in the previous embodiment illustration and examples. It is realized that these are not to be construed as limiting the scope of the invention but as merely providing illustrations of some of the presently preferred embodiments of this invention. The person skilled in the art may make various modifications and changes without departing from the scope and spirit of the present invention.

What is claimed is:

1. A method for detecting the degree of malignancy in tumors noninvasively, comprising the steps of:
   (1) using a Power Doppler ultrasound unit to scan a tumor and capture sequential color images in a complete heartbeat cycle, and choosing an area of interest (AREA_ROI) from the images;
   (2) labeling pixels reflecting signals of bloodflow in the images during one heartbeat cycle to contour an area of tumor blood vessels (AREA_vessel);
   (3) calculating a difference of PDVI between maximal systolic pressure and diastolic pressure during the heartbeat cycle to obtain tumor differential vascularity index (TDVI), and the PDVI is a ratio obtained by dividing pixels of AREA_vessel by a total area in the section of AREA_ROI; and
   (4) determining the degree of malignancy by the TDVI.

2. The method as claimed in claim 1, wherein the area of interest in tumor region (AREA_ROI) is calculated by the ultrasonic images with a depth scale.

3. The method as claimed in claim 1, wherein the method further comprises the steps of:
   (A) labeling an area of TDVI flow pixels contributed to yield tumor differential vascularity index in the pixels reflecting signals of bloodflow;

(B) calculating a total area for vessels in the tumor region during the heartbeat cycle;
(C) analyzing differences of Power Doppler signals in the area of TDVI flow pixels to calculate area of TDVI_artery and area of TDVI_vein; and
(D) combining the area of TDVI_artery and/or the area of TDVI_vein to obtain a index to determine the degree of malignancy of tumor.

4. The method as claimed in claim 3, wherein step (C) comprises analyzing and calculating a ratio of variance of pulse ($\sigma$) to mean of pulse ($\mu$) of the Power Doppler signal in the area of TDVI flow pixels during the heartbeat cycle, labeling a vessel as an artery if the ratio is larger than a predetermined threshold value while labeling the vessel as a vein when the correlation coefficient is lower than the threshold, and calculating indices of TDVI areas of arteries (TDVI_artery) and TDVI areas of veins (TDVI_vein).

5. The method as claimed in claim 3, wherein the step (C) further comprises using a blood pressure detecting device for measuring arterial pulse waveforms of tumor providing arteries, analyzing a correlation between waveform change of Power Doppler signal intensity and arterial pulse waveform in the area of TDVI flow pixels, labeling a vessel as an artery when the correlation coefficient is higher than a predetermined threshold while labeling the vessel as a vein when the correlation coefficient is lower than the threshold, and calculating indices of TDVI areas of arteries (TDVI_artery) and TDVI areas of veins (TDVI_vein).

6. The method as claimed in claim 5, wherein the Power Doppler images and the arterial pulse waveforms are recorded and analyzed synchronously.

7. The method as claimed in claim 5, wherein the arterial pulse waveforms is a blood pressure pulse waveform in upstream peripheral artery of tumor tissue.

8. The method as claimed in claim 5, wherein the arterial pulse waveform is a Power Doppler signal waveform of artery supplying for the tumor.

9. The method as claimed in claim 5, wherein the blood pressure detecting device is an air bag device for blood pressure pulse measuring.

10. The method as claimed in claim 3, wherein the index in step (D) is an arterial Vessel Density Ratio (TDVR_artery), which is calculated from dividing the area of tumor blood vessels (AREA_vessel) by TDVI areas of arteries.

11. The method as claimed in claim 3, wherein the index in step (D) is a venous Vessel Density Ratio (TDVR_vein), which is calculated from dividing the area of tumor blood vessels (AREA_vessel) by TDVI areas of veins.

12. The method as claimed in claim 1, wherein the method comprises the steps of:
(a) labeling an area of TDVI flow pixels contributed to yield tumor differential vascularity index among the image pixels reflecting signals of bloodflows;
(b) calculating a total area for vessels in the tumor region during the heartbeat cycle;
(c) calculating the neovascular area by analyzing Power Doppler signals in the area of TDVI flow pixels; and
(d) combining neovascular area to obtain an index to determine the degree of malignancy of tumor.

13. The method as claimed in claim 12, wherein the step (C) further comprises using a blood pressure detecting device for measuring the arterial pulse waveforms of tumor providing arteries, analyzing a correlation between waveform change of Power Doppler signal intensity and arterial pulse waveform in the area of TDVI flow pixels, and labeling a vessel as an angiogenesis vessel when the correlation coefficient is higher than a predetermined threshold, and calculating an index representing a neovascular area (AREA_angio).

14. The method as claimed in claim 13, wherein the Power Doppler images and the arterial pulse waveforms are recorded and analyzed synchronously.

15. The method as claimed in claim 13, wherein the arterial pulse waveforms is a blood pressure pulse waveform in upstream peripheral artery of tumor tissue.

16. The method as claimed in claim 13, wherein the arterial pulse waveform is a Power Doppler signal waveform of artery supplying for the tumor.

17. The method as claimed in claim 13, wherein the blood pressure detecting device is an air bag device for blood pressure pulse measuring.

18. The method as claimed in claim 12, wherein step (c) comprises analyzing a spectrum of Power Doppler waveform in TDVI flow pixels area, labeling a vessel as an angiogenesis vessel if a ratio of the first harmonic frequency to total pulsation energy is larger than a predetermined threshold, and calculating a neovascular area (AREA_angio).

19. The method as claimed in claim 12, wherein step (c) comprises analyzing the maximal changing rate in a time unit of Power Doppler waveform in TDVI flow pixels area, labeling a vessel as an angiogenesis vessel if the maximal changing rate is larger than a predetermined threshold, and calculating a neovascular area (AREA_angio).

20. The method as claimed in claim 12, wherein the index in step (d) is Angiogenesis Index (AI), which is a ratio of the neovascular area (AREA_angio) to the area of tumor section (AREA_ROI).

21. The method as claimed in claim 12, wherein the index in step (d) is Angiogenesis Vessel Density Ratio (AVDR), which is a ratio of the neovascular area (AREA_angio) to the area of tumor blood vessels (AREA_vessel).

22. The method as claimed in claim 1, wherein the method further comprises a resistance coefficient of tumor blood fluid mechanics to determine the degree of tumor malignancy.

23. The method as claimed in claim 22, wherein the resistance coefficient is calculated from a ratio of a timing of diastolic notch to a timing of total heartbeat cycle through an analysis of waveform of Power Doppler Intensity changes in arteries.

* * * * *